United States Patent [19]

Jones et al.

[11] Patent Number: 4,477,446
[45] Date of Patent: Oct. 16, 1984

[54] 1-BENZAZEPINES AND THEIR PHARMACEUTICAL USES

[75] Inventors: Howard Jones, Ossining; Stephen M. Coutts, Scarsdale, both of N.Y.

[73] Assignee: USV Pharmaceutical Corporation, Tarrytown, N.Y.

[21] Appl. No.: 509,616

[22] Filed: Jul. 1, 1983

[51] Int. Cl.³ .................... A61K 31/55; C07D 223/16
[52] U.S. Cl. ............................ 424/244; 260/239.3 B; 260/239 BB
[58] Field of Search .................. 260/239.3 B, 239 BB; 424/244

[56] References Cited

FOREIGN PATENT DOCUMENTS 49-28754  7/1947  Japan ........................... 260/239.3 B

OTHER PUBLICATIONS

A. H. Rees, "J. Chem. Soc.", (1959), pp. 3111H–3116H.
James and Rees, "J. Med. and Pharm.", (Chem. 5), (1962), pp. 1234H–1238H.
Misiti et al., "Tetrahedron Letters", (1965), No. 16, pp. 1071–1074.

Primary Examiner—Robert T. Bond

[57] ABSTRACT

Pharmaceutical compositions comprising 1-benzazepinediones of the formula:

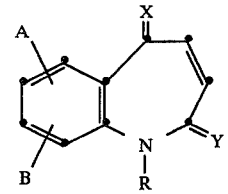

wherein:
  X and Y are independently O, S, NR or CH-R;
  A and B are independently H, halo, OH, OR, $CF_3$ or R; and
  R is H, lower alkyl, aryl, aralkyl or aminoalkyl, are useful as antiallergic agents.

15 Claims, No Drawings

1-BENZAZEPINES AND THEIR PHARMACEUTICAL USES

BACKGROUND OF THE INVENTION

(1) Field of the Invention

This invention relates to novel pharmaceutical compositions based on 1-benzazepinediones as well as to novel compounds and methods of effecting therapeutic activities, namely antiallergic and anti-asthmatic.

(2) Description of the Prior Art

Various related compounds are known in the chemical literature, some of which are said to be useful as intermediates for further chemical synthesis. Two compounds, namely 2, 3, 4, 5-tetrahydro-7,8-dimethyl-2,5,-dioxobenz(f)-azepine ane 4-(p-dimethylaminophenylamino)-2,5-dihydro-6,7-dimethyl-2,5-dioxobenz(f)azepine (J. Med. & Pharm. Chem. 5,1234A, 1962) have been shown to have antitumor activity.

The compound 1-benz(f)azepine-2,5-dione is described by R. W. Richards and R. M. Smith, Tetrahedron Letters, 22:2361 (1966), but without any specifics whatsoever as to specific utility as a pharmaceutical composition or method of administration.

The compound 2,5-dihydro-7,8-dimethylbenz(f)-azepine-2,5-dione was synthesized by A. H. Rees, J. Chem. Soc., 3111–3116 (1959).

DETAILED DESCRIPTION OF THE INVENTION

The pharmaceutical compositions of this invention comprise compounds of formula

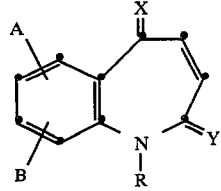

wherein:
X and Y are independently O, S, NR or CH-R;
A and B are independently H, halo, OH, OR, CF$_3$ or R; and
R is H, lower alkyl, aryl, aralkyl or aminoalkyl.

The alkyl group in lower alkyl, aralkyl and aminoalkyl preferably contains 1 to 4 carbon atoms such as methyl, ethyl, n-propyl, isopropyl, n-butyl or isobutyl.

The aryl group preferably contains 6 to 14 carbon atoms, such as phenyl, 1- or 2-naphthyl.

As indicated, two of the compounds of the formula are known, but not taught or suggested for antiallergic utilization namely, 1H-benz(f)azepine-2,5-dione and 2,5-dihydro-7,8-dimethylbenz(f)azepine-2,5-dione.

The new compounds of the present invention can be prepared by art-recognized procedures from known starting materials and intermediates. For example, all of the starting materials and some of the intermediates may be purchased from Aldrich Chemical Colmpany, Milwaukee, Wis. A schematic representation of the synthesis of dihydrobenzazepines having the designation:

X=O, S, NR, CH-R
Y=O, S
A, B=H, halo, OH, OR, CF$_3$, R
R=H, lower alkyl, aryl, aralkyl, aminoalkyl is as follows:

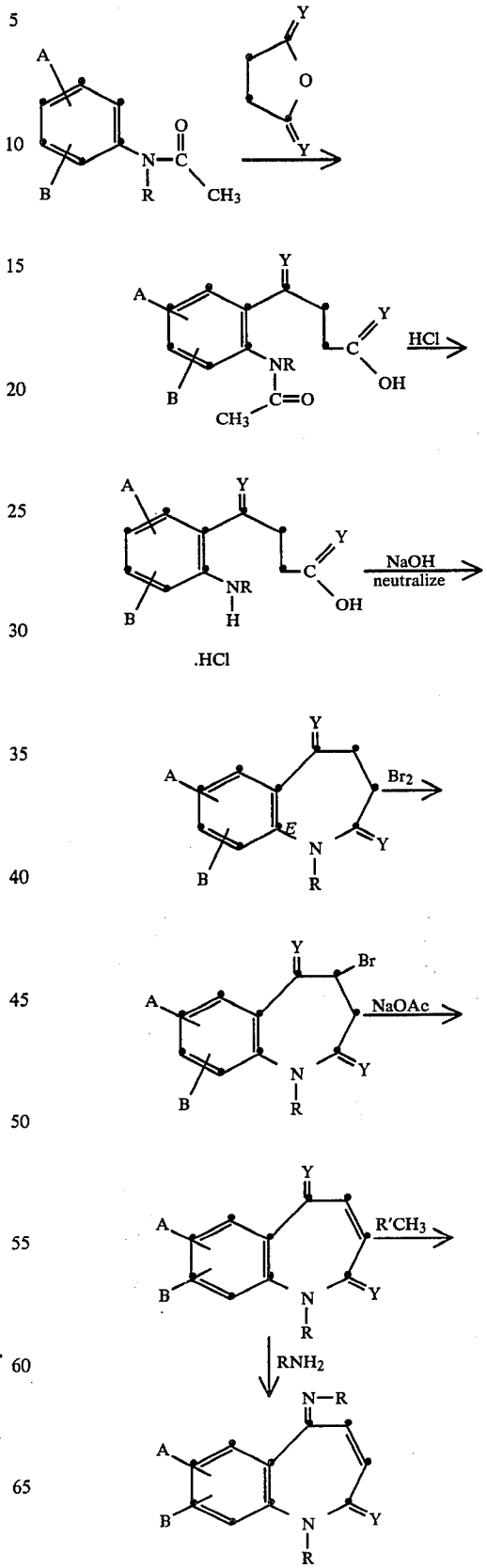

-continued

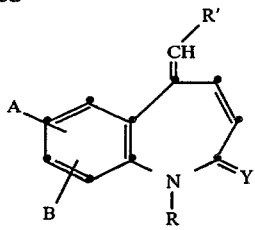

The invention will be more fully illustrated in the examples that follow. These examples are given by way of illustration and are not to be considered as limiting.

EXAMPLE 1

1H-Benz(f)azepine-2,5-dione

The compound was made according to the method of R. W. Richards and R. M. Smith, Tetrahedron Letters, 22:2361 (1966):

To a solution of 0.1 mole of 1,4-naphthoquinone in 5 ml concentrated $H_2SO_4$ at 0° C. was added, 0.1 mole of sodium azide in small portions. The mixture was then poured into a mixture of ice and water and precipitated. The precipitated compound was then filtered off and washed with water and benzene. The compound was purified by crystallization from aqueous ethanol giving 80% yield of 1H-benz(f)azepine-2,5-dione, m.p. 222°–223° C.

EXAMPLE 2

2,5-Dihydro-7,8-dimethylbenz(f)azepine-2,5-dione

The compound was made according to the method of A. H. Rees, J. Chem. Soc., 3111–3116 (1959).

A. To a suspension of succinic anhydride (30 g) in carbon disulfide (350 ml) was added N-acetyl-3,4-xylidine (32.6 g). Powdered aluminum chloride (200 g) was then added with stirring. After the initial reaction had subsided the mixture was refluxed until a dark red complex was formed. The supernatant liquor was decanted and the residue decomposed with ice, dilute hydrochloric acid, and wet benzene. Filtration left 2-β-carboxypropionyl-4,5-dimethylacetanilide which was triturated with benzene, then water, and dried to give 26.4 g (50%); mp 179° C. (from aqueous alcohol).

B. The crude 2-β-carboxypropionyl-4,5-dimethyl acetanilide (28.7 g) was refluxed for 3 hrs with 6N-hydrochloric acid (110 ml). Charcoal (0.5 g) was added and after filtration the hydrochloride monohydrate of 2-β-carboxypropionyl-4,5-dimethylaniline (20.2 g), mp 172° C. was obtained.

C. The HCl salt of 2-β-carboxypropionyl-4,5-dimethyl analine (17.7 g) was ground in a mortar with addition of 1N-sodium hydroxide until the pH rose to 7–8. After being collected and washed with water the free 2-β-carboxypropionyl-4,5-dimethylaniline (13.7 g), mp 137° C. (f.m. aqueous alcohol) was obtained.

D. A mixture of 2-β-carboxypropionyl-4,5-dimethyl aniline (16.2 g) in tertralin (55 ml) was refluxed for 6½ min. On cooling 2,3,4,5-tetrahydro-7,8-dimethyl-2,5-dioxobenz(f)azepine crystallized (13 g), mp 199° C. (from tetrahydrofuran).

E. Chloroform solution of brome (0.25 ml) and 2,3,4,5-tetrahydro-7,8-dimethyl-2,5-dixoxbenz(f)azepine (1 g) were mixed and when the color had faded the solution was concentrated at 40° C. Benzene was then added and after decantation from some tar, the solution was rapidly washed until neutral, dried and set aside to give 4-bromo-2,3,4,5-tetrahydro-7,8-dimethyl-2,5-dioxobenz(f)azepine, mp 135° C. (decomposition)

F. To a chloroform solution of the 4-bromo-2,3,4,5-tetrahydro-7,8-dimethyl-2,5-dioxobenz(f)azepine was added hydrated sodium acetate. On shaking, filtration, and storage, yellow 2,5-dihydro-7,8-dimethylbenz(f)azepine-2,5-dione, mp 258° C. (from propanol) was deposited.

In like manner as in Example 2, using appropriate starting materials and reagents, the following compounds can be made:

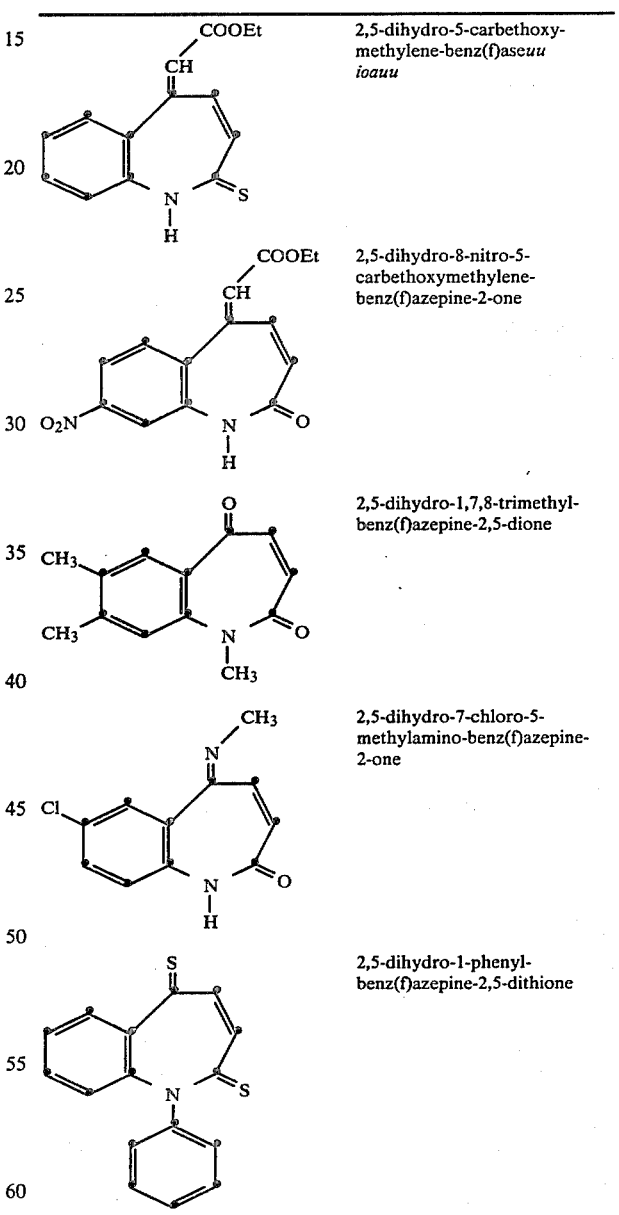

It has been found that compounds of the present invention possess valuable pharmacological properties, namely they are capable of inhibiting the binding of IgE to mast cells, and inhibiting histamine release from rat mast cells, human basophils, and from guinea pig lung slices. The compounds can, therefore, be used as an active ingredient in medicaments in human and veterinary medicine for administration, e.g. to mammals including humans. In another aspect, the invention relates to a method of treating allergy and preventing asthmatic symptoms in mammals by administering one of said compounds to said mammals in a suitable dosage form alone or together with at least one excipient or auxiliary and, if appropriate, in combination with one or more additional active compounds.

Description of biological assays conducted on a representative compound of the present invention, namely 1H-benz(f)azepine-2,5-dione, and results obtained follow.

Binding of IgE to Mast Cells 1H-benz(f)azepine-2,5-dione was found to inhibit the binding of immunoglobulin E (IgE) to mast cells. IgE is a class of antibodies playing an essential role in hypersensitivity conditions such as anaphylaxis, hay fever and asthma. These conditions are characterized by IgE antibodies binding to the surface of mast cells and basophils. When stimulating antigens intrude into the body they bind to the antibodies. The resulting antigen-antibody interaction stimulates the cells to produce histamine and other substances that cause allergic reactions. Consequently, an inhibition of IgE binding reduces and/or eliminates allergic reactions.

The test used to determine this activity was the method of S. M. Coutts et al. (Journal of Pharm. Sci., 68:353 (1979)). Briefly described, the method is as follows:

IgE, isolated from the ascitic fluid of a transplantable rat IgE immunocytoma, was labeled with iodine-125 under mild conditions employing the Bolton-Hunter reagent. The antibody was incubated with mixed peritoneal cells at 37° C., and the cell-bound IgE was separated from unbound label by sedimentation through an 8% sucrose-polymer solution in microsediment tubes. Conditions for the interaction of 3nM IgE with $3 \times 10^5$ mast cells in 150 $\mu$l were: incubation time, 2 hrs; pH, 6.5–7.0; and ionic strength, equivalent to 150 mM NaCl. Mixed peritoneal cells bind IgE with an affinity equal to that of purified mast cells.

Upon testing the compound of the present invention in a series of experiments, the following results were obtained:

In two experiments at a concentration of 30 $\mu$M, an average of 70% inhibition of IgE binding was achieved.

While complete (100%) inhibition was not achieved with any concentration of the compound, the concentration at which 50% inhibition was observed ($I_{50}$) was 12 $\mu$M.

When a fixed number of mast cells was treated with increasing concentrations of IgE, both in the absence and presence of 30 $\mu$M of the test compound, the test compound substantially lowered the affinity with which the antibody bound to its cellular receptor without changing the number of receptor sites available at infinite antibody concentration, namely, from an affinity constant $K_A$ of $4.4 \times 10^8 M^{-1}$ in control samples to an apparent $K_A$ of $0.94 \times 10^8 M^{-1}$ in samples treated with the test compound. (Scatchard Analysis, Journ. of Pharma. Sci. 68:353:357, 1979).

Inhibition of Histamine Release from Rat Mast Cells

The compound of the present invention was also tested for inhibition of histamine release from rat mast cells by the method of Khandwala et al., Int. Archs Allergy appl. Immun. 69:159–168 (1982). Rat peritoneal mast cells contain receptors for IgE antibodies as well as granules which contain preformed mediators of anaphylaxis. Immunologically stimulated secretion of histamine from these cells has long been used as a model for testing antiallergic drugs. The standard asthma prophylactic drug disodium cromoglycate is a potent inhibitor in this model. A brief summary of the method is as follows:

Freshly harvested rat peritoneal mast cells were passively sensitized in vitro with rat anti-ovalbumin serum. Spontaneous histamine release or SR (in the absence of antigen) and anaphylactically-induced histamine release or AIR (in the presence of antigen) were measured after 15 minutes of incubation. Both the histamine released into the incubation medium and the residual histamine extracted from rat mast cells were measured fluorometrically.

When 1H-benz(f)azepine-2,5-dione was added simultaneously (at 0 minutes) with antigen to the sensitized mast cells, it inhibited 50% of the antigen-induced secretion of histamine ($I_{50}$) at a concentration of 1.8 $\mu$M.

When the cells and the drug were preincubated for 5 minutes before adding antigen, the drug had an $I_{50}$ of 5 $\mu$M. In comparison the standard antiallergic compound disodium cromoglycate had an $I_{50}$ of 3 $\mu$M at 0 minutes and was inactive with 5 minutes preincubation. The rapid loss of inhibitory activity of disodium cromoglycate as a function of time of preincubation with sensitized mast cells is said to be a manifestation of its tachyphylactic property. The compound of the present invention is able to inhibit antigen-induced release of histamine from sensitized mast cells as well as prevent the sensitization of the mast celled by IgE antibodies.

Inhibition of Histamine Release from Human Basophils 1H-benz(f)azepine-2,5-dione was also tested by a method which measures inhibition of histamine release from human basophils. The basophil is a circulating granulocyte that contains preformed mediators of anaphylaxis. These mediators are secreted after immunological stimulation of the IgE-$F_c$ receptor system. The human basophil has thus been employed as a model cell system for asthma and allergy. The effect of the compound upon anti-IgE-medicated secretion of histamine from human basophils prepared from venous blood was carried out according to Siraganian, R. and Brodsky, M. J., Automated Histamine Analysis for in vitro testing, J. Allergy Clin. Immunol. 57:525–540 (1976). The summary of the method follows:

A fraction containing basophils was isolated by allowing freshly drawn human blood to sediment in the presence of dextran, saline and ethylenediamine tetraacetate. Cells obtained from the supernatant (plasma) layer were washed with buffer and were challenged to release histamine by anti-human IgE. Both the histamine secreted after the challenge and that remaining in the cells were determined by an automated fluorometric assay. The influence of 1H-benz(f)azepine-2,5-dione on anti-IgE-induced release of histamine (AIR) was assessed by preincubation of the cells with the test compound for 5 minutes before immunological challenge. The test compound was dissolved in DMSO. The final concentration of DMSO was 0.25% and did not affect spontaneous release of histamine (SR) or AIR. The results were expressed as the percent inhibition of AIR or as $I_{50}$ value.

1H-benz(f)azepine-2,5-dione was found to inhibit anti-IgE-induced secretion of histamine from human basophils over a wide concentration range. The calculated concentration at which 50% of the histamine-release was inhibited was 2 μM. The compound of the present invention is thus a potent inhibitor of histamine release in this in vitro model of human allergy and asthma.

Inhibition of Histamine Release from Guinea Pig Lung Slices 1H-benz(f)azepine-2,5-dione was also found to inhibit histamine-release from guinea pig lung slices over a wide concentration range. Immunologically mediated secretion of histamine from guinea pig lung slices is mediated through the IgG$_1$ class of antibodies, as opposed to the IgE-class of antibodies which control secretion from rat mast cells. The affect of the compound of the present invention on antigen-induced release of histamine from passively sensitized guinea pig lung slices was determined according to the procedure of Khandwala et al., Int. Archs. Allergy Appl. Immunol. 59:34–44(1979). A brief description of the method follows:

Guinea pig lung slices were passively sensitized in vitro with guinea pig anti-ovalbumin serum. Spontaneous histamine release (SR) (in the absence of antigen) and anaphylactically induced histamine release (in the presence of antigen) from these passively sensitized lung slices was measured after 15 minutes incubation. Both the histamine released into the incubation media and the residual histamine extracted from the lung slices were measured fluorometrically. Both spontaneous and antigen-induced histamine releases were expressed as % of total extractable histamine in the lung slices. Net antigen-induced histamine release (AIR) was obtained by subtracting the spontaneous release from that in the presence of the antigen. The effect of the test compound on both SR and AIR was determined following 5 minutes preincubation of sensitized lung slices with the test compound. The concentration of the test compound required for 50% inhibition of AIR (I$_{50}$) was determined.

The concentration at which 50% of the antigen-induced histamine-release was inhibited (I$_{50}$) was 20 μM.

As can be readily ascertained from the foregoing, the compounds of the present invention are effective in inhibiting the interaction of antibodies and cells believed to participate in causing allergic reactions, as well as inhibiting the allergic secretion of histamine from histamine-containing cells. As such, the compound of the present invention may be used in preventive treatment of the human or animal body and in combating diseases, in particular several forms of allergic and asthmatic diseases, specifically asthma bronchiale, allergic bronchitis, asthmatic bronchitis, food allergy, hay fever allergic rhinitis and allergic conjunctivitis.

In general, the substance of this invention is administered in analogy to known, commercially available formulations with a similar indication, such as disodium cromoglycate (Cromolyn or Intal®), in dosages of approximately 1 to 200 mg per dosage unit or higher. The daily dosage is approximately 0.02–5 mg/kg of body weight. It is to be understood, however, that the particular dose for each patient as usual depends on very diverse factors, such as the age, body weight, general condition of health, sex, diet, and the like of the patient, on the time and route of administration, or the rate of excretion, on the combination of medicaments and on the severity of the particular disease to which the therapy relates.

The compounds of the present invention may be administered enterally, parenterally or topically. The compound may be incorporated into pharmaceutical formulations having excipients suitable for these administrations and which do not adversely react with the compounds, for example, water, vegetable oils, certain alcohols and carbohydrates, gelatin, magnesium stearate, talc, cornstarch or petroleum jelly. The pharmaceutical formulations containing may be made into: tablets, capsules, elixirs, drops or supositories for enteral administration; solutions, suspensions or emulsions for parenteral administration; ointments, creams or powders for topical applications; and inhalation capsules, sprays, nasal and eye drops.

Having described the invention, it will be apparent to one of ordinary skill in the art that changes and modifications can be made thereto without departing from the spirit and scope of the invention as set forth herein.

What is claimed is:

1. A compound of the formula

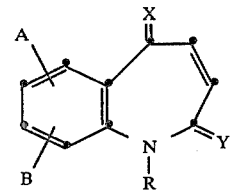

and pharmaceutically acceptable salts thereof wherein:
X and Y are independently S, NR, or CH-R;
A and B are independently halo, OH, OR, CF$_3$ or R; and
R is lower alkyl having 2 to 4 carbon atoms, aryl having 6 to 14 carbon atoms, aralkyl or aminoalkyl wherein the alkyl groups contain 1 to 4 carbon atoms.

2. The compound of claim 1 wherein said alkyl group is methyl, ethyl, n-propyl, isopropyl, n-butyl or isobutyl.

3. The compound of claim 1 wherein said aryl group is phenyl, 1- or 2-naphthyl.

4. An antiallergic composition comprising as the active ingredient a member of the formula.

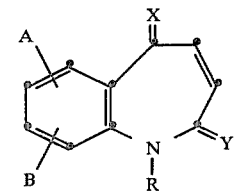

and pharmaceutically acceptable salts thereof, wherein:
X and Y are independently S, NR or CH-R;
A and B are independently halo, OH, OR, CF$_3$ or R; and
R is lower alkyl having 2 to 4 carbon atoms, aryl having 6 to 14 carbon atoms, aralkyl or aminoalkyl wherein the alkyl groups contain 1 to 4 carbon atoms in a pharmaceutically acceptable carrier.

5. A method of treating allergic conditions in a mammal which comprises administering to said mammal an effective amount for the treatment of allergic conditions of the composition of claim 4.

6. The method of claim 5 wherein said composition is administered to said mammal in a dosage form in a pharmaceutically acceptable diluent.

7. A method of treating allergic conditions in a mammal which comprises administering to said mammal an effective amount for the treatment of allergic conditions a compound of the formula

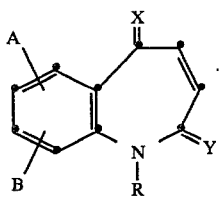

wherein
X and Y are independently O;
A and B are independently H or CH$_3$; and
R is H.

8. The method of claim 7 wherein said compound is 1H-benz(f)azepine-2,5-dione.

9. The method of claim 8 wherein said 1H-benz(f)azepine-2,5-dione is administered to said mammal in a unit dosage form.

10. The method of claim 9 wherein said 1H-benz(f)azepine-2,5-dione is administered to said mammal in a dosage form in a pharmaceutically acceptable diluent.

11. The method of claim 8 wherein said 1H-benz(f)azepine-2,5-dione is enterally administered to said mammal.

12. The method of claim 8 wherein said 1H-benz(f)azepine-2,5-dione is parenterally administered to said mammal.

13. The method of claim 8 wherein said 1H-benz(f)azepine-2,5-dione is topically administered to said mammal.

14. A method of inhibiting the interaction between antibodies and cells in a mammal which comprises administering to said mammal an effective amount for inhibiting the interaction between antibodies and cells 1H-benz(f)azepine-2,5-dione or a pharmaceutically acceptable salt thereof.

15. A method of inhibiting allergic secretion of histamine in a mammal which comprises administering to said mammal an effective amount for inhibiting allergic secretion of histamine 1H-benz(f)azepine-2,5-dione or a pharmaceutically acceptable salt thereof.

* * * * *